United States Patent
Maalouf et al.

(10) Patent No.: US 10,373,452 B2
(45) Date of Patent: Aug. 6, 2019

(54) TARGETED HAPTIC PROJECTION

(71) Applicant: Immersion Corporation, San Jose, CA (US)

(72) Inventors: Johnny Maalouf, Laval (CA); Robert W. Heubel, San Leandro, CA (US)

(73) Assignee: IMMERSION CORPORATION, San Jose, CA (US)

( * ) Notice: Subject to any disclaimer, the term of this patent is extended or adjusted under 35 U.S.C. 154(b) by 0 days.

(21) Appl. No.: 15/362,921

(22) Filed: Nov. 29, 2016

(65) Prior Publication Data
US 2018/0151035 A1    May 31, 2018

(51) Int. Cl.
| | | |
|---|---|---|
| A61N 7/00 | (2006.01) | |
| G08B 6/00 | (2006.01) | |
| G06F 3/01 | (2006.01) | |
| A63F 13/28 | (2014.01) | |

(52) U.S. Cl.
CPC ............... G08B 6/00 (2013.01); G06F 3/016 (2013.01); G06F 3/017 (2013.01); *A61N 7/00* (2013.01); *A61N 2007/0004* (2013.01); *A63F 13/28* (2014.09)

(58) Field of Classification Search
CPC combination set(s) only.
See application file for complete search history.

(56) References Cited

U.S. PATENT DOCUMENTS

| | | | |
|---|---|---|---|
| 8,884,927 B1 | 11/2014 | Cheatham, III et al. | |
| 2010/0066512 A1* | 3/2010 | Rank | G06F 3/016 340/407.2 |
| 2014/0306866 A1* | 10/2014 | Miller | G06T 19/006 345/8 |
| 2015/0192995 A1* | 7/2015 | Subramanian | G06F 3/016 340/407.1 |
| 2015/0227610 A1 | 8/2015 | Chowdry et al. | |
| 2015/0277610 A1 | 10/2015 | Kim et al. | |
| 2015/0364018 A1* | 12/2015 | Mirov | G08B 25/016 340/407.1 |
| 2017/0168630 A1* | 6/2017 | Khoshkava | G06F 1/163 |

OTHER PUBLICATIONS

Extended European Search Report for EP Appl. No. 17001697.6 dated Mar. 22, 2018.
B. Long et al., "Rendering Volumetric Haptic Shapes in Mid-Air Using Ultrasound", Proceedings of ACM SIGGRAPH Asia 2014. ACM Transactions on Graphics, 33(6), [181].
Communication pursuant to Article 94(3) EPC issued in European Application No. 17001697.6, dated Mar. 13, 2019.

* cited by examiner

Primary Examiner — Nabil H Syed
Assistant Examiner — Cal J Eustaquio
(74) Attorney, Agent, or Firm — Medler Ferro Woodhouse & Mills PLLC (57) ABSTRACT

A system provides haptic functionality. The system determines a location of a body area of a user relative to a location of a haptic device that includes an ultrasound emitter. The system then determines a haptic effect, and projects the haptic effect to the body area of the user by the ultrasound emitter of the haptic device.

20 Claims, 9 Drawing Sheets

TARGETED HAPTIC PROJECTION

FIELD

One embodiment is directed generally to a haptic system, and in particular, to a system that provides projected haptic functionality.

BACKGROUND INFORMATION

"Haptics" relates to a tactile and force feedback technology that takes advantage of the sense of touch of a user by applying haptic feedback effects (i.e., "haptic effects"), such as forces, vibrations, and motions, to the user. Devices, such as mobile devices, touchscreen devices, and personal computers, can be configured to generate haptic effects. In general, calls to embedded hardware capable of generating haptic effects (such as actuators) can be programmed within an operating system ("OS") of the device. These calls specify which haptic effect to play. For example, when a user interacts with the device using, for example, a button, touchscreen, lever, joystick, wheel, or some other control, the OS of the device can send a play command through control circuitry to the embedded hardware. The embedded hardware then produces the appropriate haptic effect.

SUMMARY

One embodiment is a system that provides haptic functionality. The system determines a location of a body area of a user relative to a location of a haptic device that includes an ultrasound emitter. The system then determines a haptic effect, and projects the haptic effect to the body area of the user by the ultrasound emitter of the haptic device.

DETAILED DESCRIPTION

One embodiment provides projected haptic functionality for contextualized haptic feedback and/or notifications. In one embodiment, one or more non-contact haptic devices (e.g., devices that provide haptic effects using ultrasound) are used to project haptic effects to a user. In some embodiments, projected haptic effects may be associated with a notification related to, for example, a message, a service, or an alert that needs to be provided to the user. In some alternative or additional embodiments, projected haptic effects may be used for gaming, muscle stimulation, smart haptics activation (e.g., changing the actuation state of "smart material actuators" that are flexible, deformable actuators such as piezoelectric, electroactive polymer ("EAP"), shape memory alloy ("SMA"), ionic polymer metal composite ("IPMC"), etc.), virtual reality interactions, guidance for the visually impaired, therapeutic massage, etc.

Figure 1:
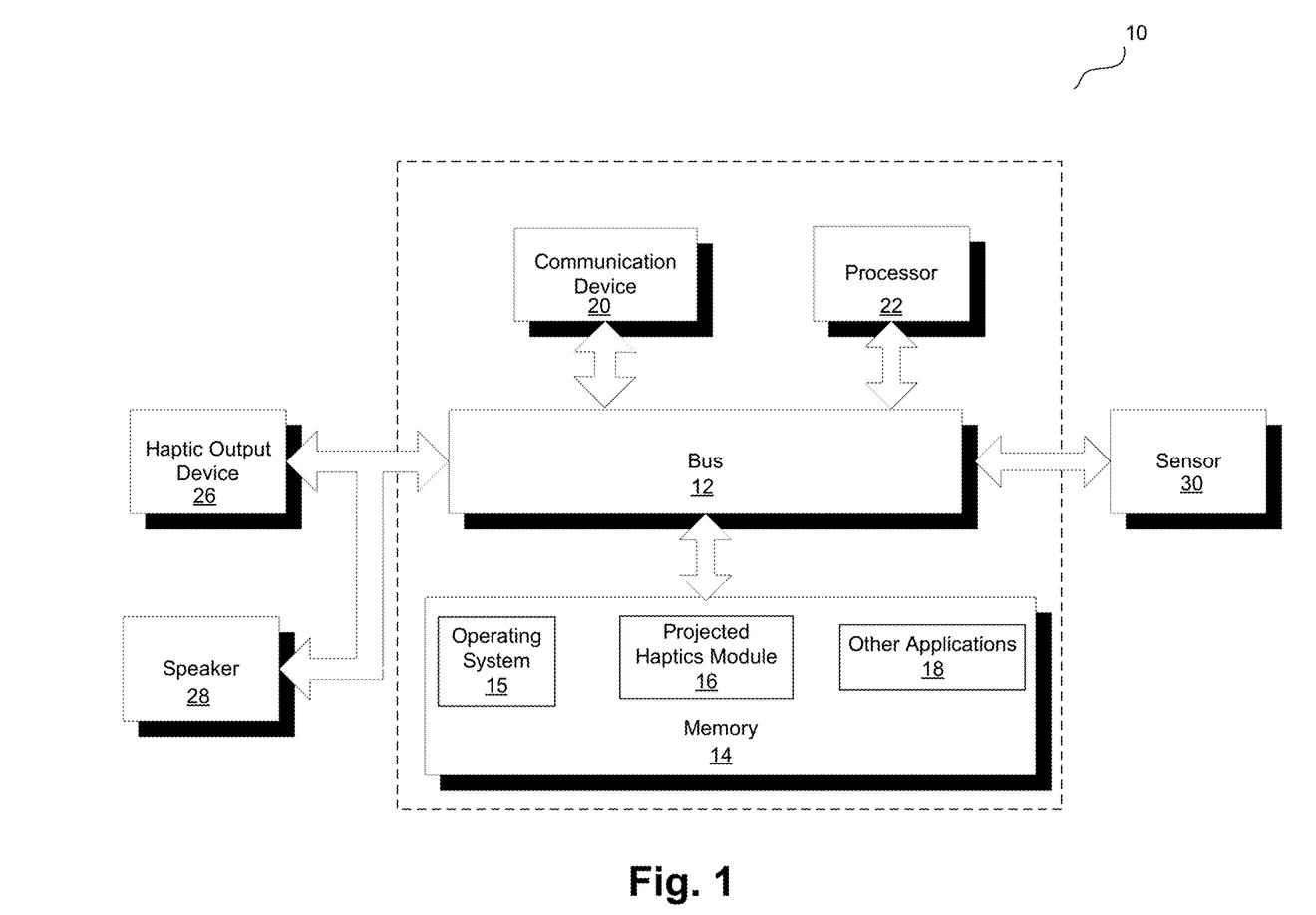
FIG. 1 is a block diagram of a computer server/system in accordance with an embodiment of the present invention.

FIG. 1 illustrates a block diagram of a system 10 in accordance with one embodiment of the invention. In one embodiment, system 10 is part of a device that provides projected (non-contact based) haptic functionality. In one embodiment, the device projects haptic effects to a user without being in physical contact with the user.

Although shown as a single system, the functionality of system 10 can be implemented as a distributed system. System 10 includes a bus 12 or other communication mechanism for communicating information, and a processor 22 coupled to bus 12 for processing information. Processor 22 may be any type of general or specific purpose processor. System 10 further includes a memory 14 for storing information and instructions to be executed by processor 22. Memory 14 can be comprised of any combination of random access memory ("RAM"), read only memory ("ROM"), static storage such as a magnetic or optical disk, or any other type of transitory or non-transitory computer-readable medium.

A computer-readable medium may be any available transitory or non-transitory medium that can be accessed by processor 22 and may include both a volatile and non-volatile medium, a removable and non-removable medium, a communication medium, and a storage medium. A communication medium may include computer-readable instructions, data structures, program modules, or other data in a modulated data signal such as a carrier wave or other transport mechanism, and may include any other form of information delivery medium known in the art. A storage medium may include RAM, flash memory, ROM, erasable programmable read-only memory ("EPROM"), electrically erasable programmable read-only memory ("EEPROM"), registers, hard disks, removable disks, compact disk read-only memory ("CD-ROM"), or any other form of a storage medium known in the art.

In one embodiment, memory 14 stores software modules that provide functionality when executed by processor 22. The modules include an operating system 15 that provides operating system functionality for system 10, as well as the rest of a mobile device in one embodiment. The modules further include a projected haptics module 16 that provides projected haptic functionality, as disclosed in more detail herein. In certain embodiments, projected haptics module 16 may comprise a plurality of modules, where each module provides specific individual functionality for providing projected haptic effects. System 10 typically includes one or more additional application modules 18 to include additional functionality, such as TouchSense™ software by Immersion Corp.

System 10, in embodiments that transmit and/or receive data from remote sources, further includes a communication device 20, such as a network interface card, to provide mobile wireless network communication, such as infrared, radio, Wi-Fi, cellular network communication, etc. In other embodiments, communication device 20 provides a wired network connection, such as an Ethernet connection, a modem, etc.

System 10 further includes a haptic output device 26 that projects haptic effects by emitting ultrasound waves. Generally, ultrasound waves are sound waves with frequencies higher than the upper audible limit of human hearing. Some ultrasound devices operate with frequencies from 20 kHz up to several gigahertz. In one embodiment, haptic output device 26 includes a transducer array (or emitter array) for transmitting ultrasonic waves. The transducer array may be a linear array, a convex array, a parametric array, a matrix array, a phased array, an acoustic array, or any other transducer array known in the art and capable of transmitting ultrasonic waves. The elements of the transducer array may include piezoelectric transducers, capacitive micromachined transducers ("CMUTs"), or any other array elements known in the art and capable of transmitting ultrasonic waves. In such embodiments, modules 18 may include additional functionality for generating ultrasound drive signals to generate ultrasound-based haptic effects as disclosed herein.

Further, in other alternate embodiments, system 10 may not include haptic output device 26, and a separate device from system 10 includes a haptic output device that generates projected haptic effects, and system 10 sends generated haptic signals to that device through communication device 20.

System 10, in one embodiment, further includes a speaker 28. Processor 22 may transmit an audio signal to speaker 28, which in turn outputs audio effects. Speaker 28 may be, for example, a dynamic loudspeaker, an electrodynamic loudspeaker, a piezoelectric loudspeaker, a magnetostrictive loudspeaker, an electrostatic loudspeaker, a ribbon and planar magnetic loudspeaker, a bending wave loudspeaker, a flat panel loudspeaker, a heil air motion transducer, a plasma arc speaker, a digital loudspeaker, etc. In alternate embodiments, system 10 may include one or more additional speakers, in addition to speaker 28 (not illustrated in FIG. 1). Further, in other alternate embodiments, system 10 may not include speaker 28, and a separate device from system 10 includes a speaker that outputs the audio effects, and system 10 sends audio signals to that device through communication device 20.

System 10, in one embodiment, further includes a sensor 30. Sensor 30 may be configured to detect a form of energy, or other physical property, such as, but not limited to, sound, movement, acceleration, biological signals, distance, flow, force/pressure/strain/bend, humidity, linear position, orientation/inclination, radio frequency, rotary position, rotary velocity, manipulation of a switch, temperature, vibration, visible light intensity, etc. Sensor 30 may further be configured to convert the detected energy, or other physical property, into an electrical signal, or any signal that represents virtual sensor information. Sensor 30 may be any device, such as, but not limited to, an accelerometer, a galvanic skin response sensor, a capacitive sensor, a hall effect sensor, an infrared sensor, an ultrasonic sensor, a pressure sensor, a fiber optic sensor, a flexion sensor (or bend sensor), a force-sensitive resistor, a load cell, a LuSense CPS2 155, a miniature pressure transducer, a piezo sensor, a strain gauge, a hygrometer, a linear position touch sensor, a linear potentiometer (or slider), a linear variable differential transformer, a compass, an inclinometer, a magnetic tag (or a radio frequency identification ("RFID") tag), a rotary encoder, a rotary potentiometer, a gyroscope, an on-off switch, a temperature sensor (such as a thermometer, thermocouple, resistance temperature detector, thermistor, temperature-transducing integrated circuit, etc.), a microphone, a photometer, an altimeter, a biological monitor, a camera, a light-dependent resistor, etc., or any device that outputs an electrocardiogram, an electroencephalogram, an electromyograph, an electrooculogram, an electropalatograph, or any other electrophysiological output.

In alternate embodiments, system 10 may include one or more additional sensors, in addition to sensor 30 (not illustrated in FIG. 1). In some of these embodiments, sensor 30 and the one or more additional sensors may be part of a sensor array, or some other type of collection/arrangement of sensors. Further, in other alternate embodiments, system 10 may not include sensor 30, and a separate device from system 10 includes a sensor that detects a form of energy, or other physical property, and converts the detected energy, or other physical property, into an electrical signal, or other type of signal that represents virtual sensor information. The device may then send the converted signal to system 10 through communication device 20.

Generally, some known systems provide non-haptic alerts to users. For example, in some known systems, a non-haptic alert mechanism such as an alarm clock or a change in the ambience lighting is used for waking a sleeping user. However, such alerts may not be effective enough for waking some users. Also, such alerts may adversely affect other users that are in the vicinity of the intended user (e.g., a sleeping spouse or child next to the intended user).

In contrast to the known systems, embodiments of the present invention use non-contact haptic devices to provide targeted haptic effects intended only for a specific user. Some embodiments quietly direct contextual haptic effects to a specific user (or group of users) without disturbing a secondary user (or group of users) that is in close proximity. Embodiments project haptic effects, and therefore do not require a haptic output device that is embedded in a device/object that is in contact with the user, such as a handheld device (e.g., a controller or mobile phone), a wearable (e.g., a watch or fitness band) or furniture (e.g., a bed or chair). One embodiment applies ultrasound vibrations to a user by focusing ultrasound patterns on specific areas of the body of the user. The areas may be detected through image recognition or any other similar functionality known in the art. Accordingly, embodiments can provide projected haptic effects targeted at a specific area of the body of a user.

In various embodiments, a projected haptic pattern targeted at a specific body area of a user may, for example, silently provide an alarm to nudge a user to wake them from sleep, alert the user to an incoming communication (e.g., a phone/video call, a message, etc.), simulate a reaction to events in a game (e.g., feeling environmental elements such as wind, feeling interactions in the game such as buttons clicking or switches activating, feeling changes in a player state such as taking damage or powering up the player's health or shields, etc.), massage the specific body area of the user, provide guidance to a visually impaired user, render haptic effects to the user while watching media, etc.

In some embodiments, for example, in order to wake a user, bed covers may be induced to generate electrostatic haptic effects to a specific area of the body of the user (and not another user that is nearby). Similarly, haptic actuators may be embedded in a bed or pillow to provide haptic effects (e.g., vibration effects) to wake the user. However, the embedded actuators and/or the resulting haptic effects may be uncomfortable for the user. Further, such alert systems are not remote systems, thereby not providing the comfort, flexibility, durability, or any other benefits of a remote system. In contrast, ultrasound-based haptic effects may be generated and projected from a remote location to the user, and hence do not cause discomfort to the user.

In some embodiments, for example, in gaming or virtual reality systems, directed puffs of air may be used to provide haptic effects to a user. However, these systems are usually noisy and therefore undesirable to some users. In contrast, ultrasound-based haptic effects may be generated and projected silently.

Some embodiments may use water therapy technology to apply feedback to a user without disturbing a secondary user that is in close proximity. For example, hot/cold water may be applied to massage a user without affecting another nearby user. However, these embodiments are only applicable to aquatic environments. In contrast, ultrasound-based haptic effects may be generated and projected in non-aquatic environments.

Generally, a parametric array may be used for transmitting ultrasonic waves. A parametric array is an array of transducers that provides nonlinear transduction to generate narrow, nearly side lobe-free beams of low frequency sound, through the mixing and interaction of high frequency sound waves, effectively overcoming the diffraction limit associated with linear acoustics. The main side lobe-free beam of low frequency sound is created as a result of nonlinear mixing of two high frequency sound beams at their difference frequency. As such, a transducer may project a narrow beam of modulated ultrasound that is powerful enough (e.g., at 100 to 110 dBSPL) to substantially change the speed of sound in the air that it passes through. The air within the beam behaves nonlinearly and extracts the modulation signal from the ultrasound, resulting in sound that can be heard only along the path of the beam, or that appears to radiate from any surface that the beam strikes. This allows for a beam of sound to be projected over a long distance and be heard only in a small well-defined area such that a listener outside the beam hears nothing. Such ultrasound transmission of sound is also referred to as hypersonic sound.

Embodiments may further include a Time Reversal Mirror ("TRM") that can focus waves using Time Reversal Signal Processing. Time Reversal Signal Processing may be used for focusing waves such as ultrasound. Time reversal is based on the reciprocity of the wave equation: given a solution to the wave equation, the time reversal (using a negative time) of that solution is also a solution. Time reversal can be modeled as a matched filter. If a delta function is the original signal, then the received signal at the TRM is the impulse response of the channel. The TRM sends the reversed version of the impulse response back through the same channel, effectively auto-correlating it. This autocorrelation function has a peak at the origin where the original source was.

In one embodiment, a parametric array may be used for transmitting ultrasonic waves that cause a haptic sensation on a body area of a user, and a TRM may be used to focus the ultrasonic waves on the body area of the user. In various embodiments, any known system may be used to implement ultrasound technology to provide haptic effects, for example, as disclosed in "B. Long, S. A. Seah, T. Carter and S. Subramanian, Rendering Volumetric Haptic Shapes in Mid-Air Using Ultrasound, Volume 33, Issue #7 of ACM Transactions on Graphics (Siggraph Asia) 2014." Some known systems provide haptic feedback in free space by using multiple ultrasound speakers to make changes in the air pressure around a user. This provides the ability to feel the pockets of air pressure focused in the environment, and give the user tactile cues for gestures, invisible interfaces, textures, virtual objects, etc. A focal point may be created by triggering ultrasound transducers with specific phase delays so that all sound waves arrive at the focal point concurrently. The ultrasound may be modulated so that it is perceived as a vibration on the skin. Changing the modulation frequency or pulsing the feedback may simulate different textures. By giving each feedback point a different modulation frequency, different feedback with different textures may be applied to the user at the same time.

Generally, the pressure caused by sound received at a location is referred to as sound pressure and is measured in decibels (dB) per octave bands. In some embodiments, measures of ultrasound pressure received at a certain area on the body of a user are used to design and project haptic effects to the user and cause a haptic pattern (e.g., tapping, nudging, pushing, massaging, etc.). In some embodiments, a haptic pattern may cause the movement of pulsed patterns across parts of the body to give the sensation of motion of the patterns across the skin.

In one embodiment, haptic effects are projected using focused ultrasonic signals. For example, an acoustic lens may be used to precisely and accurately concentrate multiple intersecting beams of ultrasound on a target (e.g., a body area of a user), and haptic effects may result at the target of the focused ultrasound pulses (e.g., a tapping or nudging sensation).

In one embodiment, haptic effects are projected by constructive interference of ultrasound/acoustic pulses. Constructive interference happens when two waves meet in such a way that their crests line up. In one embodiment, ultrasound emitters are configured to provide ultrasound waves that constructively interfere at a targeted location on a body area of a user, thus causing haptic sensations in that body area.

In some embodiments, passive tactile experience is provided to a user that interacts with a virtual object in space. For example, projected haptic effects may allow a user to feel the edges/perimeter of a virtual shape in mid-air. However, some embodiments provide active tactile experience to a user by applying projected haptic effects such as haptic effects generated by ultrasound where the sound patterns are directed to give a user a tactile experience without the user having to interact with a virtual object in space.

One embodiment provides an ultrasound haptic generating panel/device that creates ultrasound haptic shapes or patterns with variable intensity. The embodiment implements motion sensing or sound sensing functionality (e.g., using sensor 30) to detect the presence of a user and the location of body parts of the user for directing haptic effects to specific body locations. One embodiment senses more than a single user and directs the same or different haptic effects (with the same or different haptic parameters) to the same or different body locations of the users. One embodiment can connect and interface with multiple devices such as phones, smart watches, and other devices with wireless technology such as Bluetooth, WiFi, etc.

One embodiment includes an ultrasound haptic generating array that includes ultrasound emitters (or transducers) mounted to a panel or other array to generate ultrasound shapes or patterns at specific points in space. The embodiment further includes sensing functionality such as position or audio sensing (e.g., cameras, microphones, heat sensing, infrared sensing, etc.). The embodiment further includes processing functionality that analyzes the sensor feed to determine the position of the user, and a driving unit that generates a desired haptic shape at the desired position. The embodiment may further include networking functionality (e.g., using communication device 20) so that multiple ultrasound units may work in tandem and/or multiple haptic targets may receive projected haptic effects.

In some embodiments, the ultrasound haptic panels/devices can shift position/location by implementing any mechanical systems known in the art (e.g., a gear box and a motor, one or more linear actuators, etc.). Accordingly, the orientation of the panels/devices may be adjusted so that the panels and/or the resulting ultrasound waves are continuously directed toward the user or toward a specific body area of the user as the user moves or as the specific body area moves.

Generally, ultrasonic audio at certain frequencies and magnitudes can be harmful to the human body, for example, as disclosed in "Effects of Ultrasonic Noise on the Human Body—A Bibliographic Review, International Journal of Occupational Safety and Ergonomics (JOSE) 2013, Vol. 19, No. 2, 195-202". As such, one embodiment reduces any potentially harmful effects of ultrasound to users. One embodiment tracks the user position and motion and adjusts the haptic parameters of the ultrasound pulses based on the tracking information so that the ultrasound pulses are not directed at sensitive body areas (e.g., eyes) and the ultrasound pulses are not at intensities that can produce damaging thermal effects.

For example, one embodiment may implement image recognition functionality to compare the images of a targeted body area of a user with one or more images of known sensitive body areas (e.g., eyes) in a look up table, and prevent ultrasound projection when a match is identified.

As another example, one embodiment may receive calculated haptic parameters of ultrasound-based haptic effects, calculate the intensity of the resulting ultrasound waves at the target of the projection, and prevent ultrasound projection when the intensity is higher than a threshold. The threshold may be different for different body areas, may be different for different users, may depend on gender, age, height, weight, or any other characteristics of the users, and/or may be configured based on user preferences. User preferences and/or identity may be configured at a haptic output device or may be determined by implementing any image recognition functionality known in the art.

In one embodiment, for example, a threshold value of the intensity of the resulting ultrasound waves at the target of the projection may correspond to a percentage of the voltage applied to the haptic output device. For example, a 100% voltage value may be configured as the high threshold value in one embodiment. In another embodiment, a high threshold value may include a range of percentages. For example, a range of 90%-100% voltage values may be configured as a high threshold value range, where different values in that range correspond to different body areas, users, genders, ages, etc.

Figure 2:
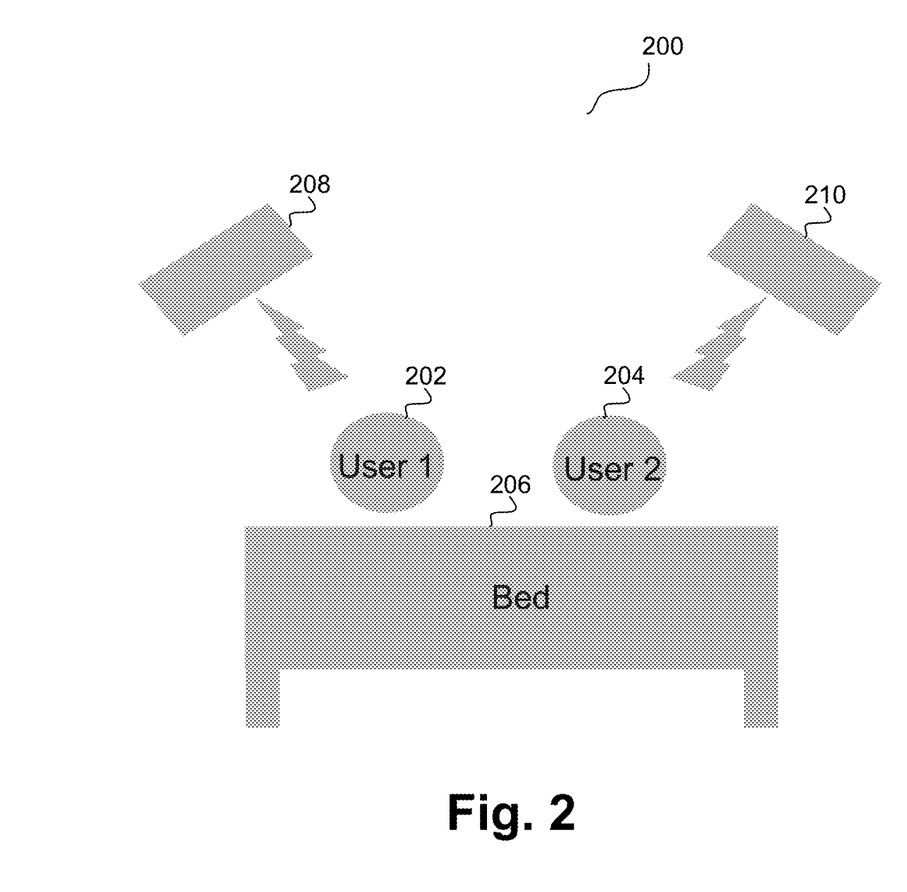
FIGS. 2-7 illustrate example systems for providing haptic functionality according to an embodiment of the present invention.

FIG. 2 is an example system 200 in one embodiment that provides haptic functionality to silently wake a first user 202 and/or a second user 204 that sleep on a same bed 206. For example, first user 202 and/or second user 204 may be heavy sleepers that do not wake up with just an alarm clock but would more easily wake up if a hand nudges their shoulder or taps on their shoulder. As such, first user 202 and/or second user 204 may implement an ultrasound platform and configure it to provide a haptic pattern to their shoulder in the form of, for example, a hand nudging their shoulder or tapping on their shoulder. For example, a first ultrasound emitter 208 may be configured to project ultrasound-based haptic effects on first user 202. Similarly, a second ultrasound emitter 210 may be configured to project ultrasound-based haptic effects on second user 204. First ultrasound emitter 208 and second ultrasound emitter 210 may be configured and operate independently and according to respective preferences of first user 202 and second user 204. The silent wake up functionality provided by system 200 for an intended user does not wake up a nearby user (e.g., a spouse or a child).

In one embodiment, system 200 may take images of a body area of first user 202 (or second user 204) and implement image recognition functionality to compare the images with one or more targeted body area images or shapes (e.g., an image or shape of a hand, a shoulder, a torso, etc.) stored in a look up table, and project ultrasound haptic effects when a match is identified. For example, when first user 202 (or second user 204) indicates preference for receiving haptic wake up alarm on a specific body area (e.g., shoulders), system 200 may be configured to search for and identify the preferred body area and project ultrasound haptic effects at that body area.

In various embodiments, the preferred body area may include parts of head and neck (e.g., face, ears, nose, forehead, etc.), parts of hands (e.g., fingers, joints, palms, backs of hands, wrists, etc.), parts of legs (e.g., hips, thighs, calves, feet, etc.), parts of feet (e.g., toes, joints, ankles, tops of feet, bottom of feet, etc.), etc. For example, for configuring a haptic wake up alarm, any body part that may be exposed during sleep may be selected as the preferred body area for ultra-sound haptic projection.

Figure 3:
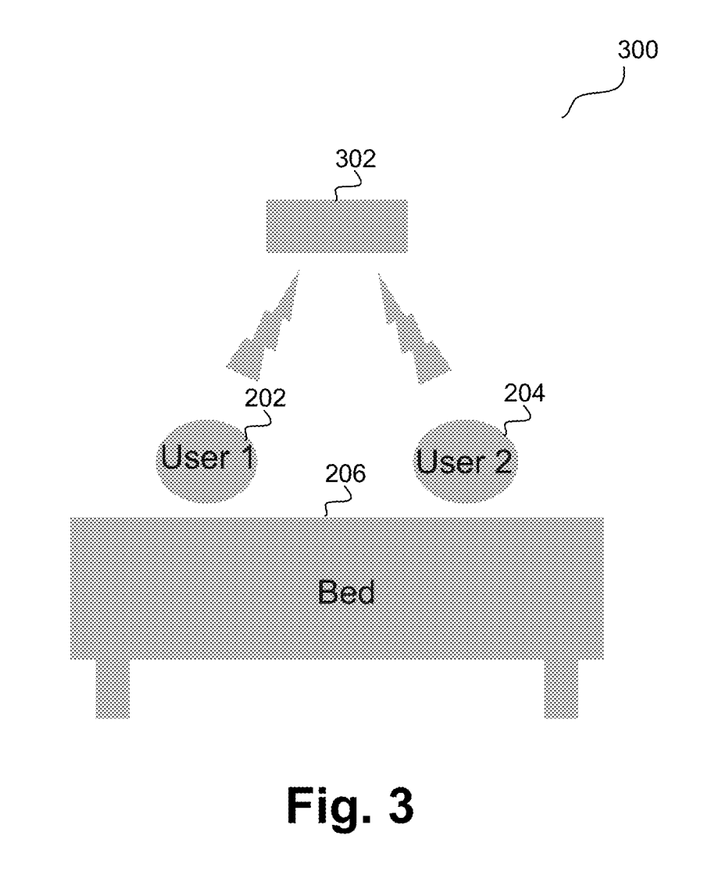

FIG. 3 is an example system 300 in another embodiment that provides haptic functionality to silently wake first user 202 and second user 204 that sleep on same bed 206. However, in system 300, a single ultrasound emitter 302 is configured to project the same or different ultrasound-based haptic effects at the same or different times on first user 202 and second user 204. Ultrasound emitter 302 may be directed toward first user 202 or second user 204 by implementing any mechanical systems known in the art (e.g., a gear box and a motor, one or more linear actuators, etc.).

Figure 4:
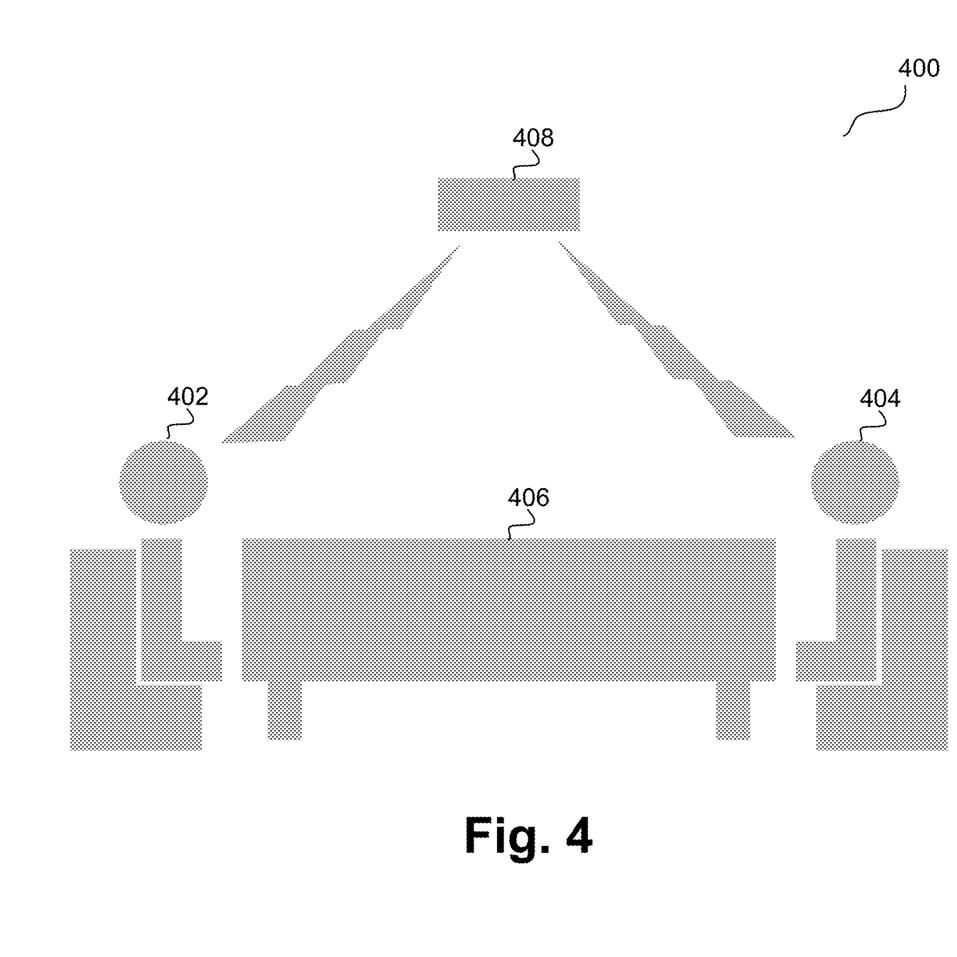

FIG. 4 is an example system 400 in an embodiment that provides haptic functionality to silently provide notifications or contextualized haptic effects to a first user 402 and/or a second user 404 that sit at a table 406 such as a conference table in a meeting room. In system 400, a single ultrasound emitter 408 is configured to project the same or different ultrasound-based haptic effects at the same or different times on first user 402 and second user 404. In one embodiment, system 400 provides notifications/alerts to first user 402 and/or second user 404 by projecting ultrasound-based haptic effects on an area of the body of first user 402 and/or second user 404. Ultrasound emitter 408 may be directed toward first user 402 or second user 404 by implementing any mechanical systems known in the art (e.g., a gear box and a motor, one or more linear actuators, etc.).

For example, in an emerging technology company where the pace of work is very fast and connectivity is critical, employees may need to stay connected even during meetings. However, notification/alarm functionalities that generate buzzing/tones may be distracting during a meeting. In contrast, system 400 may be implemented in meeting rooms such that when first user 402 and/or second user 404 walk into a meeting room, their devices automatically switch to quiet and send respective alarms/notifications to system 400 so that ultrasound emitter 408 can project corresponding haptic effects to a specific user without disturbing others in the meeting. In one embodiment, more important alerts that require immediate attention may induce different projected haptic effects, shapes, and/or intensities on individual users in the room.

Figure 5:
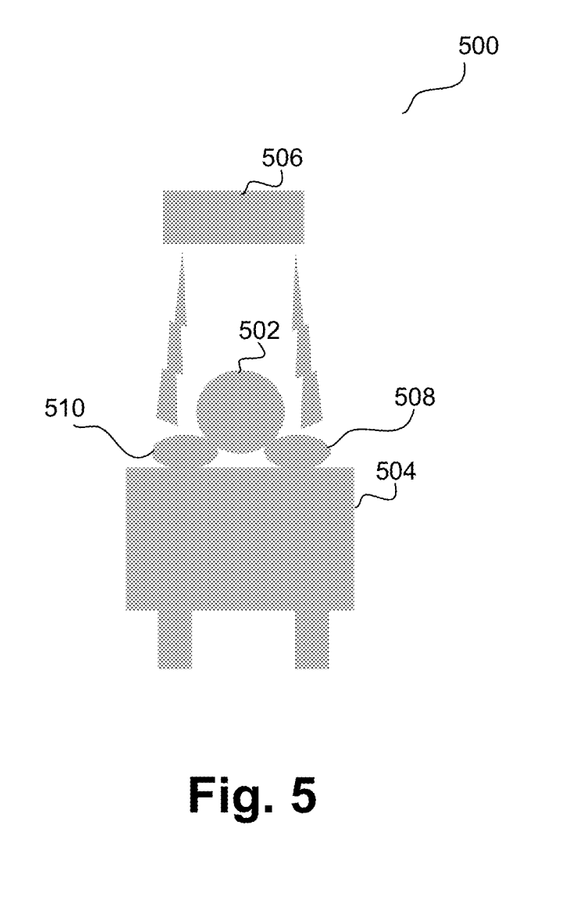

FIG. 5 is an example system 500 in an embodiment that provides haptic functionality to massage a user 502 on a massage table 504 (or chair). In system 500, an ultrasound emitter 506 is configured to project the same or different ultrasound-based haptic effects at the same or different times on a right shoulder 508, a left shoulder 510, or any other body area of user 502. Ultrasound emitter 506 may be directed toward right shoulder 508, left shoulder 510, or any other body area of user 502 by implementing any mechanical systems known in the art (e.g., a gear box and a motor, one or more linear actuators, etc.).

Generally, other massage methods such as handheld massagers or massage chairs may be used for massaging right shoulder 508 and/or left shoulder 510 of user 502. However, handheld massagers may be undesirable due to the required effort and the resulting noise. Massage chairs may also be too forceful, fail to provide focused massage on right shoulder 508 and/or left shoulder 510 according to the preferences of user 502, and result in undesirable noise. In contrast, system 500 silently projects haptic patterns to right shoulder 508 and/or left shoulder 510 of user 502 according to the preferences of user 502. The haptic patterns can be configured by user 502 to both soothe and warm the affected areas. As such, user 502 may receive a massage therapy that does not distract from other activities (e.g., watching TV) and does not disturb others in the vicinity of user 502. Further, user 502 may leave table 504 and easily resume the therapy later.

Generally, heating pads may be used to alleviate pain on right shoulder 508 and a left shoulder 510 of user 502. However, heating pads are cumbersome to wrap around right shoulder 508 and/or left shoulder 510 of user 502 and are not configurable. Further, the pads have to be unwrapped and wrapped again if user 502 needs to interrupt the therapy. In contrast, system 500 projects haptic patterns to right shoulder 508 and/or left shoulder 510 of user 502 according to the preferences of user 502. The haptic patterns can be configured by user 502 to both soothe and warm the affected areas, and user 502 may leave table 504 and easily resume the therapy later.

Figure 6:
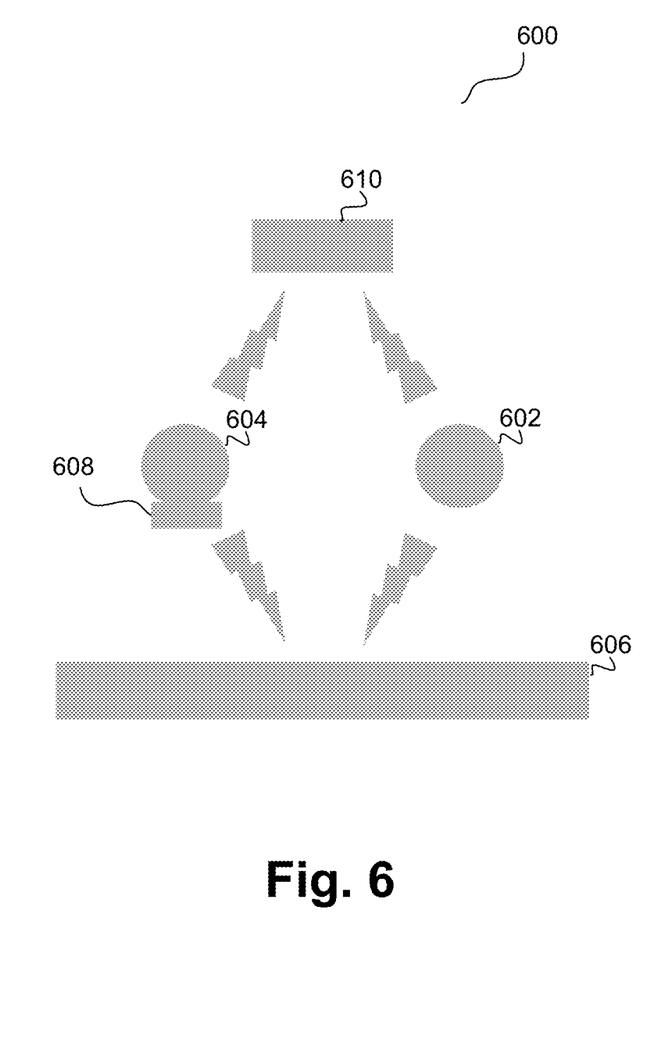

FIG. 6 is an example system 600 in an embodiment that provides haptic notifications or contextualized haptic effects to a first user 602 and/or a second user 604 that are viewing a monitor 606 (e.g., a TV or a monitor of a computer) or wearing a virtual reality headset 608 (such as the Oculus Rift). First user 602 and/or second user 604 may use monitor 606 or headset 608 to, for example, play a game, watch a movie, etc. In system 600, an ultrasound emitter 610 is mounted behind, above, or anywhere around first user 602 and second user 604 and is configured to project the same or different ultrasound-based haptic effects at the same or different times on first user 602 and second user 604. Alternatively or additionally, monitor 606 may include one or more built-in ultrasound emitters configured to project the same or different ultrasound-based haptic effects at the same or different times on first user 602 and second user 604. Ultrasound emitter 610 or built-in ultrasound emitters in monitor 606 may be directed toward first user 602 or second user 604 by implementing any mechanical systems known in the art (e.g., a gear box and a motor, one or more linear actuators, etc.).

For example, first user 602 (or second user 604) may be playing a virtual reality game and moving their hands and fingers to provide input via a controller that requires no hand contact or touching, such as a "Leap Motion" controller. Since the controller is not being touched by first user 602 (or second user 604), first user 602 (or second user 604) does not receive any haptic response that a standard hand-held game controller would have provided. However, ultrasound emitter 610 and/or built-in ultrasound emitters of monitor 606 may be configured to project haptic effects on the hands/fingers of first user 602 (or second user 604) in response to the motions sensed/perceived by a no-touch controller.

In one embodiment, first user 602 and/or second user 604 may be playing a game that provides haptic information related to a haptic effect configured for a hand-held game controller (or wearable accessories such as haptic chest pads). In this embodiment, ultrasound emitter 610 and/or built-in ultrasound emitters of monitor 606 may be configured to project haptic effects on first user 602 and/or second user 604 in response to the haptic information related to the game. In one embodiment, the haptic information may include haptic parameters configured for a contact-based actuator, and system 600 translates the haptic actuator parameters into corresponding ultrasound parameters (e.g., using a look up table), and uses the motion sensing capabilities of the no-touch controller to determine where to direct the ultrasound-based haptic effects (e.g., on hands/fingers or on another body location/area of first user 602 and/or second user 604).

In one embodiment, system 600 may be implemented to provide projected haptic effects in conjunction with media. For example, first user 602 and/or second user 604 may watch a movie on monitor 606 and may desire to receive haptic effects related to the movie content, and system 600 receives haptic information related to the movie and generates and projects corresponding ultrasound-based haptic effects to first user 602 and/or second user 604 via ultrasound emitter 610 and/or built-in ultrasound emitters of monitor 606. In one embodiment, the haptic information may include broadcast haptics designed by a media producer and may be processed by a TV (e.g., monitor 606) or any other processing unit. In an alternative or additional embodiment, system 600 may automatically generate ultrasound-based haptic effects based on inputs such as sound. In one embodiment, system 600 may project different haptic intensities or patterns to different individuals in a room depending on their user preferences.

Figure 7:
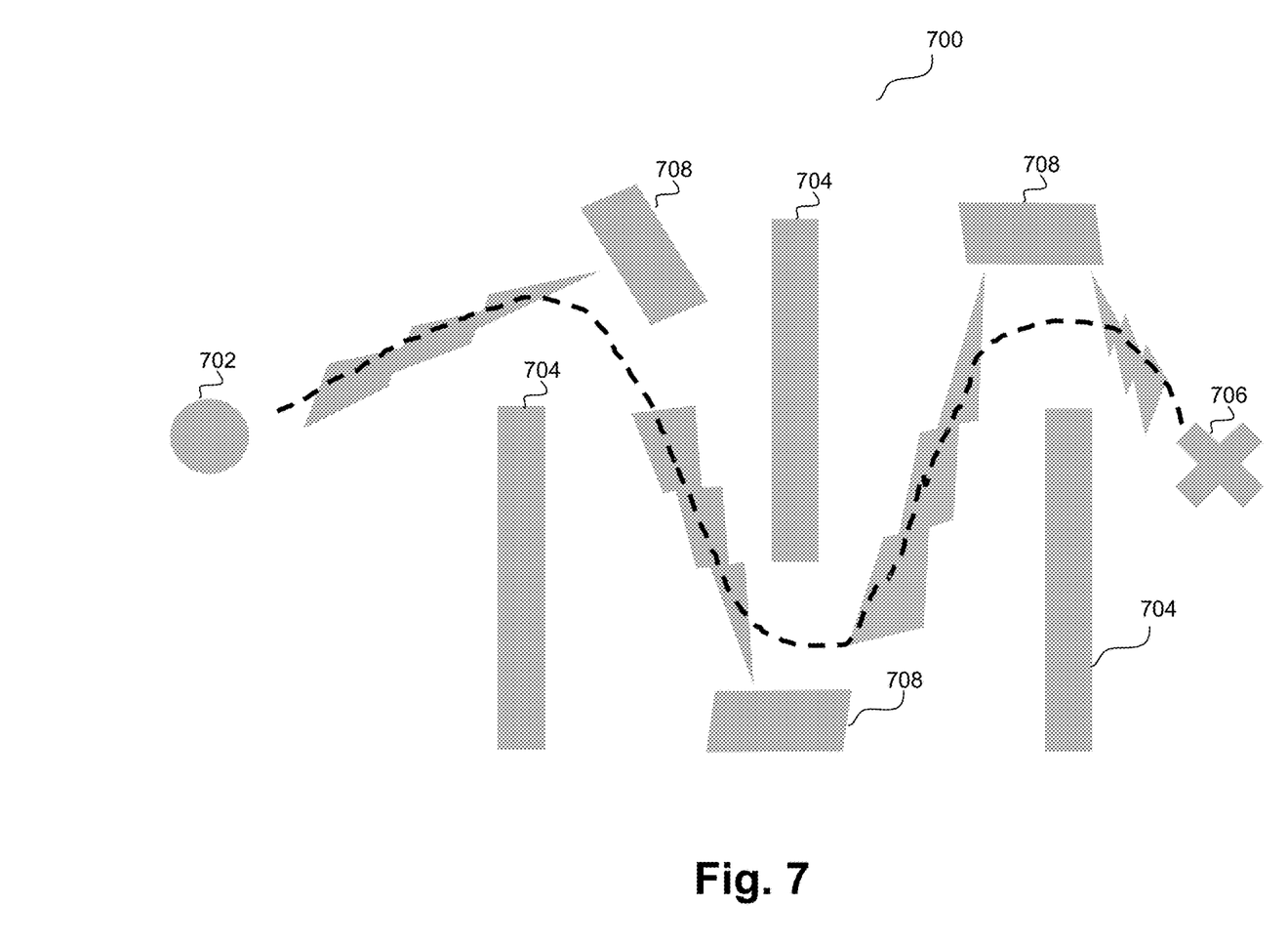

FIG. 7 is an example system 700 in an embodiment that uses one or more ultrasound emitters 708 to project haptic notifications or contextualized haptic effects to a user 702 to help user 702 navigate through one or more obstacles 704 and reach a destination 706. In one embodiment, user 702 may be a visually impaired person that needs guidance to navigate through the aisles of a store, and system 700 implements one or more ultrasound panels throughout the store to guide user 702 to a product they are looking for and/or to store services such as cashiers, customer service, rest rooms, etc. Ultrasound emitters 708 may be directed toward user 702 by implementing any mechanical systems known in the art (e.g., a gear box and a motor, one or more linear actuators, etc.).

In one embodiment, user 702 may use a device such as a mobile phone to access the functionality provided by the ultrasonic navigation network of system 700. For example, user 702 may input information that identifies the product or service they are looking for in the store, and the ultrasonic network of system 700 determines and projects a haptic navigation path for user 702 based on a current in-store location of user 702. In one embodiment, as user 702 moves through the store aisles, they feel projected haptic effects (e.g., ultrasound taps on the body) from one or more ultrasound emitters 708 that indicate in which direction to move and also keep them from running into objects or people directly in their path.

One embodiment may implement one or more ultrasound emitters in a system that supports connection to multiple user devices (e.g., personal devices such as mobile phones) and provides any combination of functionalities of systems 200, 300, 400, 500, 600, and 700. For example, a system may implement one or more ultrasound emitters in a living room to project ultrasound-based haptic effects on a user that is watching a movie, and also massage the same or a different user. As another example, a system may implement one or more ultrasound emitters in a bedroom to project ultrasound-based haptic effects to wake a user, and also massage the same or a different user at the same or at a different time.

In alternative embodiments, any non-contact haptic technology other than ultrasound-based haptics (e.g., air jets, static electrostatic friction ("ESF"), etc.) may be used in the embodiments to project haptic effects to a user. The projected haptic output may be, for example, a puff of air using an air jet, a laser-based projectile, a sound-based projectile, etc. In a laser-based projectile, laser energy ionizes air molecules in a concentrated region mid-air to provide plasma (a concentrated mixture of positive and negative particles). The laser may be a femtosecond laser that emits pulses at very fast and very intense paces, and the faster the laser, the safer for humans to touch. The projectile may appear as a hologram that is haptic and interactive. When the plasma comes in contact with user skin, the user may sense the vibrations of energized air molecules in the concentrated region. Sensations on the user skin are caused by the waves that are generated when the user interacts with plasma in mid-air. Accordingly, haptic effects may be provided to the user by subjecting the user to such concentrated region. Alternatively or additionally, haptic effects may be provided to the user by subjecting the user to the vibrations generated by directed sound energy.

In one embodiment, for non-contact based haptic devices (e.g., ultrasound haptics), the haptic device projects haptic effects to a user when it is within range of the user. In one embodiment, the haptic device is within range of a user when the user is within a certain distance of an emitter of the device and there are no obstructions between the emitter and the user. In one embodiment, a projection haptic device may be paired with one or more sensors (e.g., sensor 30 in FIG. 1) such as cameras or depth sensors that can detect the presence of a user within range of the haptic device. In one embodiment, specific body areas (e.g., shoulder) of the detected user may be determined by any known functionality (such as computer vision) and a comparison with data stored in a database to establish a match.

In one embodiment, the one or more sensors include a three dimensional ("3D") imaging system such as one or more cameras oriented toward the user to detect the user's movements. The 3D imaging system may capture images of the user and determine that a user movement occurred. The embodiment may further analyze the images to determine changed positions of specific body areas of the user.

In some embodiments, the sensors are external to the non-contact based haptic device and in wired or wireless communication with the device. For example, the sensors may include a camera associated with the device and in communication with the device. As another example, the sensors may comprise a 3D imaging system (e.g., the 3D imaging system commonly sold under the trademark Microsoft Kinect®) or an LED-based tracking system positioned external to the device and in communication with the device.

Various embodiments may provide additional and/or complementary haptic functionality in addition to ultrasound-based projected haptic functionality. For example, some embodiments may be part of or associated with a mobile device (e.g., a smartphone) or a non-mobile device, and provide haptic functionality for the device. Some embodiments may be part of or associated with a device that is incorporated into an object in contact with a user in any way (e.g., furniture), and provide haptic functionality for such a device. For example, one embodiment may be part of or associated with a wearable device such as wrist bands, headbands, eyeglasses, rings, leg bands, arrays integrated into clothing, or any other type of device that a user may wear on a body or can be held by a user. Some wearable devices can be "haptically enabled," meaning they include mechanisms to generate haptic effects. Some embodiments may be separate from the device (e.g., a mobile device or a wearable device), and remotely provide haptic functionality for the device.

Some embodiments may further include or be associated with an actuator configured to output haptic effects such as vibrotactile haptic effects, electrostatic friction haptic effects, deformation haptic effects, etc., in response to a drive signal. The actuator may be, for example, an electric motor, an electro-magnetic actuator, a voice coil, a shape memory alloy, an electro-active polymer, a solenoid, an eccentric rotating mass motor ("ERM"), a linear resonant actuator ("LRA"), a piezoelectric actuator, a high bandwidth actuator, an electroactive polymer ("EAP") actuator, etc.

Some embodiments may further include or be associated with a haptic output device that operates according to any other haptic technology such as thermal displays (e.g., hot/cold), electrotactile stimulation (i.e., stimulation of tactile receptors with electric current), kinesthetic feedback, etc. Some embodiments may implement electrical muscle stimulations such as a task that requires a user to determine what movement or movements the system is making them do or feel like doing.

Some embodiments may further include or be associated with a non-mechanical or a non-vibratory haptic output device such as a device that uses ESF or ultrasonic surface friction ("USF") or a haptic substrate and a flexible or deformable surface or shape changing device attached to a user's body, etc.

Figure 8:
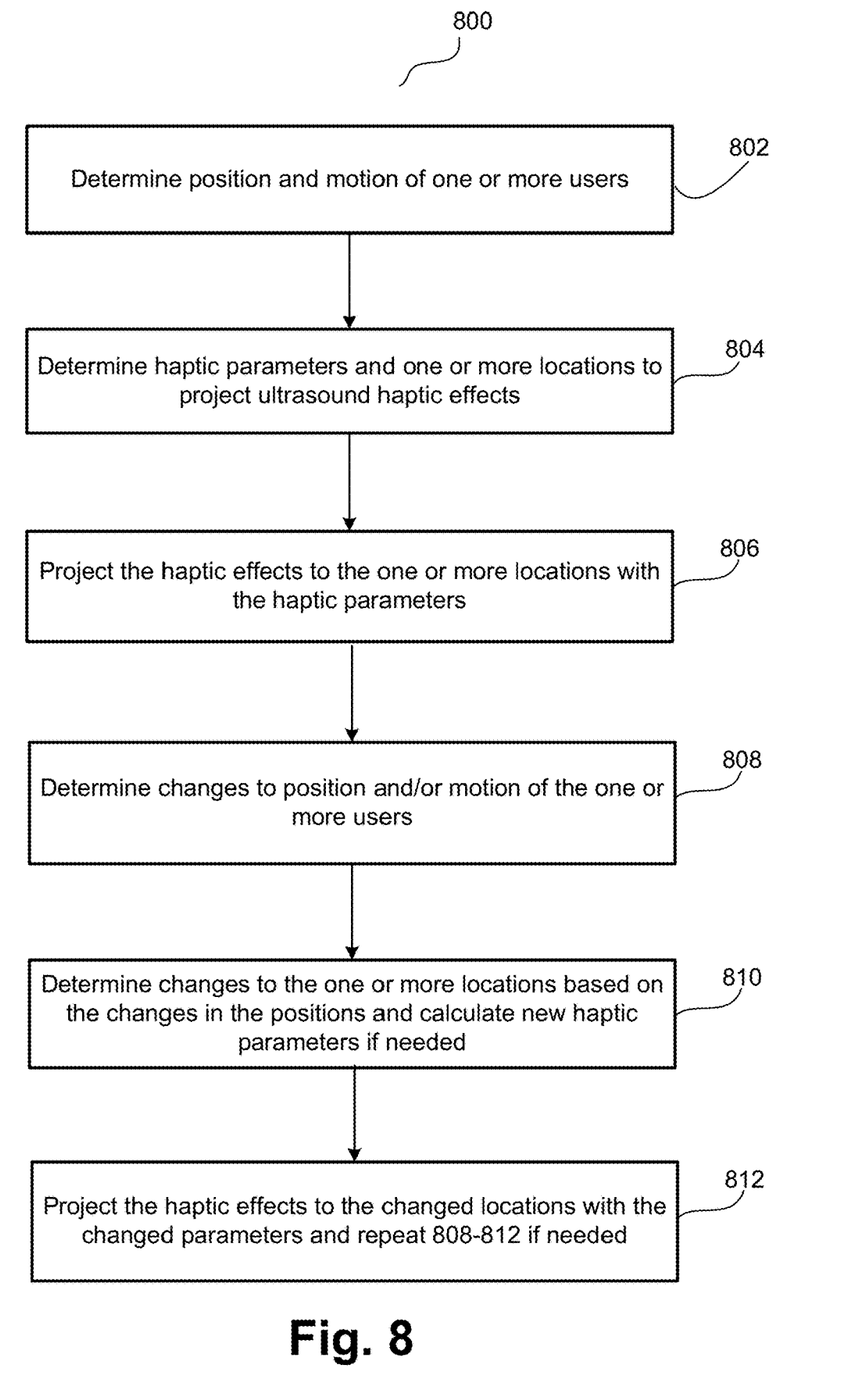
FIGS. 8 and 9 are flow diagrams of the operation of the projected haptics module of FIG. 1 when performing haptic functionality in accordance with embodiments of the present invention.

FIG. 8 is a flow diagram 800 of haptic functionality in accordance with embodiments of the present invention. In one embodiment, the functionality of the flow diagram 800 of FIG. 8 (and flow diagram 900 of FIG. 9 below) is implemented by software stored in memory or other computer readable or tangible medium, and executed by a processor. In other embodiments, the functionality may be performed by hardware (e.g., through the use of an application specific integrated circuit ("ASIC"), a programmable gate array ("PGA"), a field programmable gate array ("FPGA"), etc.), or any combination of hardware and software.

At 802 the position and motion of one or more users are determined, and at 804 haptic parameters and one or more locations to project haptic effects are determined. For example, one embodiment may calculate the distance of a user or a specific user body part from an ultrasound-based haptic output device and then calculate haptic parameters such as a direction for haptic projection, a magnitude of haptic projection corresponding to the voltage applied to the haptic output device, a type/pattern of haptic projection (e.g., a pulsed pattern), a duration of haptic projection, etc.

At 806 the haptic effects are projected to the one or more locations with the haptic parameters.

At 808 changes to position and/or motion of the one or more users are determined, and at 810 changes to the one or more locations are determined based on the changes in the position, and new haptic parameters are calculated if needed.

At 812 the haptic effects are projected to the changed location with the changed parameters. In some embodiments, 808-812 are repeated if needed.

Figure 9:
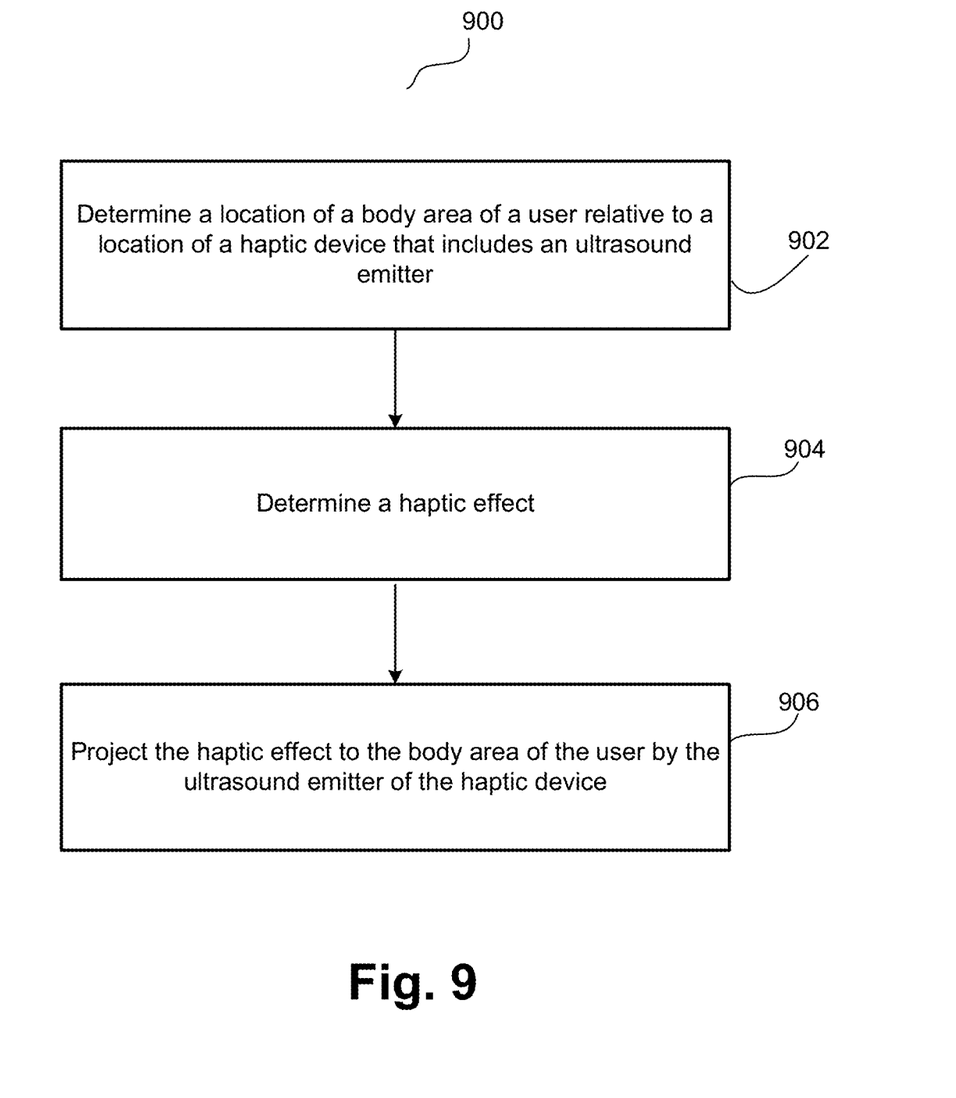

FIG. 9 is another flow diagram 900 of haptic functionality in accordance with embodiments of the present invention.

At 902 a location of a body area of a user relative to a location of a haptic device is determined. In one embodiment, the haptic device includes an ultrasound emitter. In one embodiment, the location of the body area of the user is determined based on one or more images or sounds.

At 904 a haptic effect is determined. In one embodiment, the haptic effect corresponds to a notification or an alarm intended for the user. In one embodiment, the notification or the alarm is received from a personal device of the user. In one embodiment, the haptic effect corresponds to a movement or interaction performed by the user or a multimedia provided to the user. In one embodiment, a haptic track related to the multimedia is received and corresponding haptic parameters are determined for the projectile haptic device.

At 906 the haptic effect is projected to the body area of the user by the projectile haptic device. In one embodiment, a change in the location of the body area of the user is determined, and the projecting is adjusted based on the change. In one embodiment, the adjusting includes moving the ultrasound emitter based on the change.

As disclosed, embodiments allow for silently projecting haptic effects to a specific body area of a specific user without disturbing nearby users. One embodiment projects ultrasound-based haptic effects to a targeted body area of a user. The haptic effects may provide contextualized haptic feedback and/or notifications. Embodiments may be configured according to each user's preferences. By allowing for targeted and tailored haptic effects without disturbing unintended users, embodiments allow for more desirable haptic notification.

Several embodiments are specifically illustrated and/or described herein. However, it will be appreciated that modifications and variations of the disclosed embodiments are covered by the above teachings and within the purview of the appended claims without departing from the spirit and intended scope of the invention.

What is claimed is:

1. A non-transitory computer readable medium having instructions stored thereon that, when executed by a processor, cause the processor to provide haptic functionality by:
   determining a location of a user body area relative to a location of a haptic device, wherein the haptic device comprises an ultrasound emitter;
   determining an intensity threshold associated with the user body area;
   determining a haptic effect and an intensity that the haptic effect would have at the user body area;
   projecting the haptic effect to the user body area by the ultrasound emitter of the haptic device when the intensity does not exceed the intensity threshold; and
   preventing the haptic effect from being projected to the user body area when the intensity exceeds the intensity threshold.

2. The non-transitory computer readable medium of claim 1, wherein the instructions cause the processor to provide the haptic functionality further by:
   determining a change in the location of the user body area; and
   adjusting the projecting based on the change.

3. The non-transitory computer readable medium of claim 2, wherein the adjusting comprises moving the ultrasound emitter based on the change.

4. The non-transitory computer readable medium of claim 1, wherein the location of the user body area is determined based on one or more images or sounds.

5. The non-transitory computer readable medium of claim 1, wherein the haptic effect corresponds to a notification or an alarm.

6. The non-transitory computer readable medium of claim 5, wherein the notification or the alarm is received from a communication device.

7. The non-transitory computer readable medium of claim 1, wherein the haptic effect corresponds to a user movement or user interaction or to multimedia.

8. The non-transitory computer readable medium of claim 7, wherein the determining of the haptic effect comprises:
   receiving a haptic track related to the multimedia; and
   determining corresponding haptic parameters for the haptic device.

9. A method of providing haptic functionality, comprising:
   determining a location of a user body area relative to a location of a haptic device, wherein the haptic device comprises an ultrasound emitter;
   determining an intensity threshold associated with the user body area;
   determining a haptic effect and an intensity that the haptic effect would have at the user body area; and
   projecting the haptic effect to the user body area by the ultrasound emitter of the haptic device when the intensity does not exceed the intensity threshold; and
   preventing the haptic effect from being projected to the user body area when the intensity exceeds the intensity threshold,
   wherein the user body area is one of a plurality of user body areas to which the ultrasound emitter can direct the haptic effect, wherein the plurality of user body areas are associated with different respective intensity thresholds, and wherein the intensity threshold that is determined is one of the different respective intensity thresholds.

10. The method of claim 9, further comprising:
    determining a change in the location of the user body area; and
    adjusting the projecting based on the change.

11. The method of claim 10, wherein the adjusting comprises moving the ultrasound emitter based on the change.

12. The method of claim 9, wherein the location of the user body area is determined based on one or more images or sounds.

13. The method of claim 9, wherein the haptic effect corresponds to a notification or an alarm.

14. The method of claim 13, wherein the notification or the alarm is received from a communication device.

15. The method of claim 9, wherein the haptic effect corresponds to a user movement or user interaction performed or to multimedia.

16. The method of claim 15, wherein the determining of the haptic effect comprises:
    receiving a haptic track related to the multimedia; and
    determining corresponding haptic parameters for the haptic device.

17. A system for providing haptic functionality, comprising:
    a haptic device that comprises an ultrasound emitter;
    a processor in communication with the haptic device, wherein the processor is configured
      to determine a location of a user body area relative to a location of the haptic device;
      to determine an intensity threshold associated with the user body area;
      to determine a haptic effect and an intensity that the haptic effect would have at the user body area; and to cause the ultrasound emitter of the haptic device to project the haptic effect to the user body area when the intensity does not exceed the intensity threshold; and to prevent the haptic effect from being projected to the user body area when the intensity exceeds the intensity threshold.

18. The non-transitory computer-readable medium of claim 1, wherein different user body areas are associated with different respective intensity thresholds in the non-transitory computer-readable medium.

19. The non-transitory computer-readable medium of claim 1, wherein the instructions cause the processor to select the user body area from among a plurality of user body areas.

20. The non-transitory computer-readable medium of claim 1, wherein the instructions further cause the processor to determine parameters of the haptic effect, the parameters including a direction in which to project the haptic effect from the ultrasound emitter.

* * * * *